United States Patent
Koori

(10) Patent No.: US 8,765,961 B2
(45) Date of Patent: Jul. 1, 2014

(54) NEAR INFRARED FLUORESCENT IMAGING AGENT

(75) Inventor: Hiroshi Koori, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 524 days.

(21) Appl. No.: 12/869,488

(22) Filed: Aug. 26, 2010

(65) Prior Publication Data

US 2011/0054181 A1     Mar. 3, 2011

(30) Foreign Application Priority Data

Aug. 28, 2009  (JP) ................................ 2009-197727

(51) Int. Cl.
*C07D 401/14* (2006.01)
*C07D 209/04* (2006.01)

(52) U.S. Cl.
USPC ........................................ 546/277.4; 548/455

(58) Field of Classification Search
USPC ........................................ 546/277.4; 548/455
See application file for complete search history.

(56) References Cited

U.S. PATENT DOCUMENTS

| | | | |
|---|---|---|---|
| 7,547,721 B1 | 6/2009 | Miwa et al. | |
| 2003/0180221 A1* | 9/2003 | Miwa et al. | 424/9.6 |
| 2005/0226815 A1* | 10/2005 | Kawakami et al. | 424/9.6 |

FOREIGN PATENT DOCUMENTS

| | | |
|---|---|---|
| JP | 2001-151752 A | 6/2001 |
| JP | 2002-526458 A | 8/2002 |
| JP | 2003-160558 A | 6/2003 |
| JP | 3507060 A | 12/2003 |
| JP | 2005-519977 A | 7/2005 |
| JP | 2006-513293 A | 4/2006 |
| JP | 2009-507035 A | 2/2009 |
| JP | 2009-263280 A | 11/2009 |
| JP | 2012-524153 A | 10/2012 |
| WO | 00/16810 A1 | 3/2000 |
| WO | 01/43781 A1 | 6/2001 |
| WO | 03/074091 A2 | 9/2003 |
| WO | 2004/065491 A1 | 8/2004 |
| WO | 2006/072580 A1 | 7/2006 |
| WO | 2007/005222 A2 | 1/2007 |
| WO | 2007/028118 A2 | 3/2007 |
| WO | 2010/121163 A2 | 10/2010 |

OTHER PUBLICATIONS

Grant & Hackh's Chemical Dictionary (5th Ed. 1987) at p. 148.*

Database Registry Chemical Abstracts Service, Columbus, Ohio, Accession No. RN 165186-84-5, Entered STN: Jul. 25, 1995.*

Database Registry Chemical Abstracts Service, Columbus, Ohio, Accession No. RN 1193408-81-9 and 1193408-92-2, Entered STN: Nov. 23, 2009.*

Shao, F. et al., "Monofunctional Carbocyanine Dyes for Bio- and Bioorthogonal Conjugation", Bioconjugate Chemistry, vol. 19, No. 12, pp. 2487-2491 (Dec. 17, 2008).

Oswald, B. et al., "Novel Diode Laser-compatible Fluorophores and Their Application to Single Molecule Detection, Protein Labeling and Fluorescence Resonance Energy Transfer Immunoassay", Photochemistry and Photobiology, vol. 74, No. 2, pp. 237-245 (Aug. 1, 2001).

Extended European Search Report dated Jan. 27, 2011 on EP Application No. 10174111.4.

Office Action dated Oct. 1, 2013 in Japanese Application No. 2009-197727.

Office Action dated Jan. 7, 2014 in Japanese Application No. 2009-197727.

* cited by examiner

*Primary Examiner* — Samantha Shterengarts

(74) *Attorney, Agent, or Firm* — Sughrue & Mion, PLLC

(57) ABSTRACT

A compound represented by general formula (I) below, or a pharmacologically acceptable salt thereof:

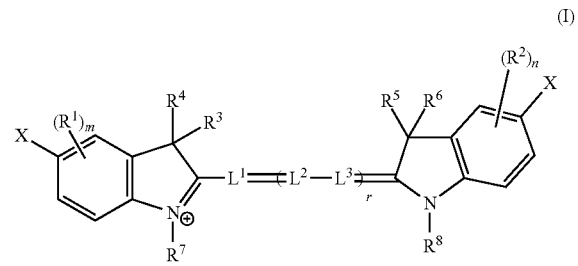

(I)

wherein X represents sulfonic acid group; $R^1$ and $R^2$ represent substituents; $R^3$ to $R^6$ represent optionally substituted alkyl groups; $R^7$ and $R^8$ represent an optionally substituted alkyl groups; $L^1$ to $L^3$ represent optionally substituted methine groups, with at least one of $L^1$ to $L^3$ being a methine group having a substituent with the bulkiness of an ethyl group or greater; r represents an integer of from 0 to 3, and when r is 2 or more, the plural $L^2$ and the plural $L^3$ may be the same or different, respectively; each of m and n independently represents an integer of 0 to 3; and at least one of the substituents is sulfonic acid group or a group comprising sulfonic acid group, which is useful as an imaging component in a near infrared fluorescence imaging agent.

4 Claims, 2 Drawing Sheets
(2 of 2 Drawing Sheet(s) Filed in Color)

NEAR INFRARED FLUORESCENT IMAGING AGENT

CROSS-REFERENCE TO RELATED APPLICATIONS

This application claims benefit of priority under 35 USC 119 to Japanese Patent Application No. 2009-197727 filed on Aug. 28, 2009, the disclosure of which is expressly incorporated by reference herein in its entirety.

TECHNICAL FIELD

The present invention relates to a near infrared fluorescence imaging agent containing a novel compound.

BACKGROUND ART

In the treatment of disease, morphological and functional changes that are caused by disease within an organism are important for detecting disease at an early stage. In the treatment of cancer, in particular, learning the position, size, and nature of a tumor early on is extremely important for determining a strategy and protocol. Examples of methods that have conventionally been employed for this purpose, in addition to biopsy by puncture and the like, are image diagnosis by X-ray imaging, MRI, PET, and ultrasound imaging. Biopsy is useful for making a diagnosis, but the burden on the patient is great and it is unsuitable for tracking the progression of lesions over time. X-ray imaging, MRI, and PET necessarily expose the patient to radiation and electromagnetic waves. Further, in conventional imaging diagnosis such as that mentioned above, complex operations and long periods are required for measurement. From the perspective of the size and shape of the device, it is difficult to perform surgery while navigating using these methods during surgical operations.

Fluorescence imaging is an imaging diagnostic method that solves these problems. In this method, a substance that generates fluorescence when exposed to stimulating light of a specific wavelength is employed as an imaging agent. Further, this method comprises the steps of irradiating an excitation beam from outside the organism and detecting the fluorescence that is released by the fluorescent material within the organism.

Cyanine compounds are typical compounds that can be used in the fluorescence imaging method. In practice, indocyanine green (abbreviated as "ICG" hereinafter) is currently employed to test liver function and in ophthalmic angiography. However, ICG dissolves readily, and must be employed in formulations to which iodine is added. There is thus a problem in that it cannot be used in patients who are allergic to iodine.

The compound (denoted as "SF-64" hereinafter) that is described in Claim 1 of Japanese Patent No. 3,507,060, the disclosure of which is expressly incorporated by reference herein in its entirety, is an example of a cyanine compound that solves this solubility problem. This dye is characterized by good solubility in water and low toxicity. It is also described in this patent as having the property of outlining tumors.

SUMMARY OF THE INVENTION

The object of the present invention is to provide a novel compound that is useful as an imaging component in near infrared fluorescence imaging agent.

The present inventors conducted extensive research on the mechanisms by which cyanine compounds accumulate in tumors using SF-64. As a result, they discovered that the cyanine compounds and the derivatives of the cyanine compounds form complexes with albumin in plasma. Based on this knowledge, they discovered a new group of cyanine compounds with actually enhanced imaging function relative to SF-64 in terms of the tumor outlining time period. The present invention was devised based on this discovery. The present invention thus provides [1] to [8] below.

[1] A compound represented by general formula (I) below, or a pharmacologically acceptable salt thereof:

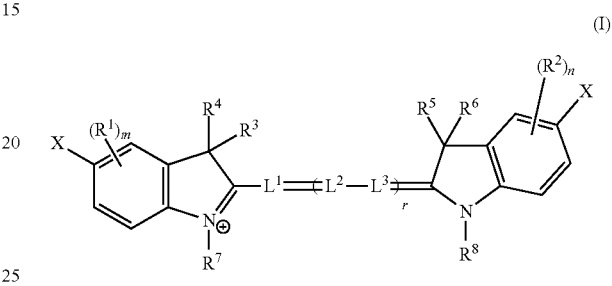

(I)

wherein X represents sulfonic acid group; each of $R^1$ and $R^2$ independently represents a substituent; $R^3$ to $R^6$ may be identical or different and each represents an optionally substituted alkyl group; each of $R^7$ and $R^8$ independently represents an optionally substituted alkyl group; $L^1$ to $L^3$ may be identical or different and each represents an optionally substituted methine group, with at least one of $L^1$ to $L^3$ being a methine group having a substituent with the bulkiness of an ethyl group or greater; r represents an integer of from 0 to 3, and when r is 2 or more, the plural $L^2$ and the plural $L^3$ may be the same or different, respectively; each of m and n independently represents an integer of 0 to 3; and at least one of the substituents is sulfonic acid group or a group comprising sulfonic acid group.

[2] The compound according to [1] represented by general formula (II) below, or a pharmacologically acceptable salt thereof:

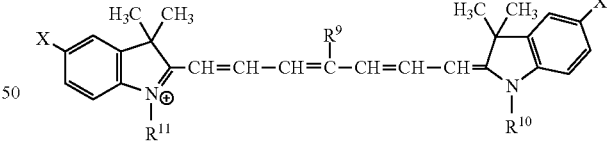

wherein each of $R^{10}$ and $R^{11}$, which may be identical or different, represents an alkyl group substituted with sulfonic acid group, carboxylic acid group, or phosphonic acid group; and $R^9$ represents an alkyl group other than methyl group, an aryl group, an arylalkyl group, a heterocyclic group, an acylamino group, an arylamino group, an N-aryl-N-alkylamino group, an arylthio group, an aryloxy group, or an acylaminoaryloxy group.

[3] The compound according to [2], or a pharmacologically acceptable salt thereof, wherein $R^9$ represents ethyl group, an aryl group, or an arylmethyl group.

[4] The compound according to any one of [1] to [3], or a pharmacologically acceptable salt thereof, wherein one or more of the acid groups form salts with sodium ions.

[5] A near infrared fluorescence imaging agent comprising the compound, or pharmacologically acceptable salt thereof, according to any one of [1] to [4].
[6] The near infrared fluorescence imaging agent according to [5], which is used to image a tumor.
[7] The near infrared fluorescence imaging agent according to [6], which is used to image a tumor of a type expressing a high level of SPARC.
[8] The near infrared fluorescence imaging agent according to [6] or [7], which is used to image tumors occurring in the mouth cavity, pharynx, digestive organs, respiratory organs, bones, joints, soft tissue, skin, breasts, genitalia, urinary system, eyes, eyeball sockets, brain, central nervous system, or endocrine system.

From additional perspectives, the present invention provides the use of the above compounds for manufacture of a fluorescence imaging agent; a fluorescence imaging method comprising the step of fluorescence imaging after administering the above compound to a mammal, including a human; and a tumor imaging method comprising the step of fluorescence imaging after administering the above compound to a mammal, including a human.

BRIEF DESCRIPTION OF DRAWINGS

The patent or application file contains at least one drawing executed in color. Copies of this patent or patent application publication with color drawings will be provided by the Office upon request and payment of the necessary fee.

MODES OF CARRYING OUT THE INVENTION

Figure 1:
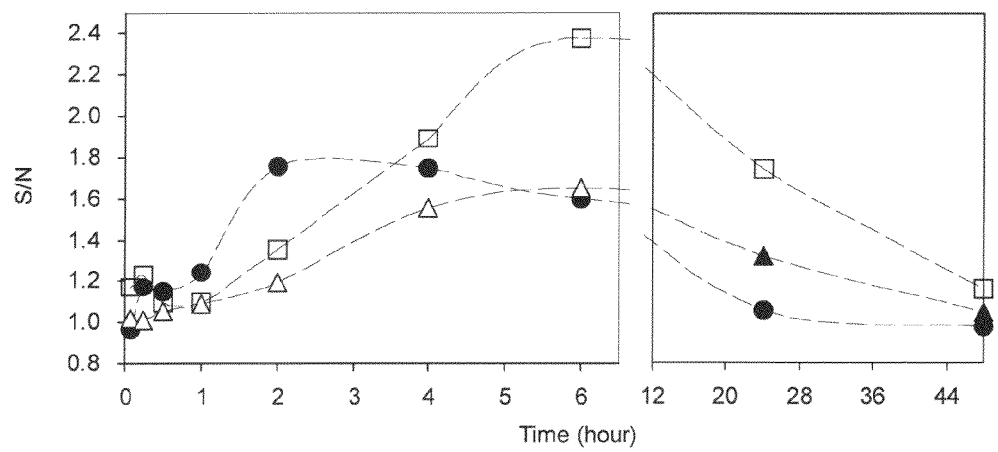
FIG. 1 is a graph showing the results of measurement of the transition over time in the ratio of the fluorescence intensity of the tumor site divided by the fluorescence intensity of the thigh portion (S/N ratio) at various points in time when compound B (●: black circle), compound 1 (□: square), and compound 3 (Δ: triangle) were administered to mice inoculated with HCT116 cells by the method described in test example 3.

In the present specification, the term "substituent," or the substituent meant by the use of the term "optionally substituted" or "substituted or unsubstituted," can be selected from the group of substituents listed below by way of example:

Substituent group: halogen atoms, alkyl groups, alkenyl groups, alkynyl groups, aryl groups, heterocyclic groups, cyano groups, hydroxyl groups, nitro groups, carboxylic acid groups (carboxyl groups), alkoxy groups, aryloxy groups, silyloxy groups, heterocyclic oxy groups, acyloxy groups, carbamoyloxy groups, alkoxycarbonyloxy groups, aryloxycarbonyloxy groups, amino groups, alkylamino groups, arylamino groups, acylamino groups, aminocarbonylamino groups, alkoxycarbonylamino groups, aryloxycarbonylamino groups, sulfamoylamino groups, alkyl and arylsulfonylamino groups, mercapto groups, alkylthio groups, arylthio groups, heterocyclic thio groups, sulfamoyl groups, sulfonic acid groups (sulfo groups), alkylsulfinyl groups, arylsulfinyl groups, alkylsulfonyl groups, arylsulfonyl groups, acyl groups, aryloxycarbonyl groups, alkoxycarbonyl groups, carbamoyl groups, arylazo groups, heterocyclic azo groups, imide groups, phosphonic acid groups (phosphoric acid groups), phosphino groups, phosphinyl groups, phosphinyloxy groups, phosphinylamino groups, and silyl groups.

Those among these groups that are capable of forming salts, and all that are capable of forming salts by dissociation of one or more hydrogen ions, may be in the form of salts. The counter ions of these salts are, for example, positive charge or negative charge that may be present in the compound of the present invention, an alkali metal ion and an alkaline earth metal ion.

Examples of the halogen atom include chlorine atom, bromine atom, and iodine atom.

Alkyl groups may be linear, branched, cyclic alkyl groups, or any combination thereof. Examples include linear alkyl groups having 1 to 30 carbon atoms (such as methyl, ethyl, n-propyl, isopropyl, t-butyl, n-octyl, eicosyl, and 2-ethylhexyl), cycloalkyl groups having 3 to 30 carbon atoms (such as cyclohexyl, cyclopentyl, 4-n-dodecylcyclohexyl), bicycloalkyl groups having 5 to 30 carbon atoms (monovalent groups obtained by removing a single hydrogen atom from a bicycloalkane having 5 to 30 carbon atoms, such as bicyclo[1,2,2]heptane-2-yl and bicyclo[2,2,2]octane-3-yl), and alkyl groups having structures with even more rings, such as tricyclo structures.

Unless specifically stated otherwise, the alkyl moieties of substituents on alkyl moieties are identical to the above alkyl groups.

Alkenyl groups may be linear, branched, or cyclic alkenyl groups. Examples include linear alkenyl groups having from 2 to 30 carbon atoms (such as vinyl, allyl, prenyl, geranyl, and oleyl), cycloalkenyl groups having 3 to 30 carbon atoms (monovalent groups obtained by removing a single hydrogen atom from a cycloalkene having 3 to 30 carbon atoms, such as 2-cyclopentene-1-yl and 2-cyclohexene-1-yl), and bicycloalkenyl groups having 5 to 30 carbon atoms (monovalent groups obtained by removing a single hydrogen atom from a bicycloalkene having a single double bond, such as bicyclo[2,2,1]hepto-2-ene-1-yl and bicyclo[2,2,2]octo-2-ene-4-yl). Preferable examples of alkynyl groups include alkynyl groups having 2 to 30 carbon atoms (such as ethynyl and propargyl). Preferable examples of aryl groups include aryl groups having 6 to 30 carbon atoms, such as phenyl, p-tolyl, and naphthyl.

Heterocyclic groups are preferably five or six-membered heterocyclic groups, and can be monovalent groups obtained by removing a single hydrogen atom from an aromatic or non-aromatic heterocyclic compound. Preferable examples include five or six-membered aromatic heterocyclic groups having 3 to 30 carbon atoms, such as 2-furyl, 2-thienyl, 2-pyrimidinyl, and 2-benzothiazolyl. Preferable examples of alkoxy groups include alkoxy groups having 1 to 30 carbon atoms, such as methoxy, ethoxy, isopropoxy, t-butoxy, and n-octyloxy. Preferable examples of aryloxy groups include aryloxy groups having 6 to 30 carbon atoms, such as phenoxy groups. Preferable examples of silyloxy groups include silyloxy groups having 3 to 20 carbon atoms, such as trimethylsilyloxy and t-butyldimethylsilyloxy.

Preferable examples of heterocyclicoxy groups include heterocyclicoxy groups having 2 to 30 carbon atoms, such as tetrazole-5-oxy and 2-tetrahydropyranyloxy. Examples of acyloxyl groups include formyloxy groups, alkylcarbonyloxy groups having 2 to 30 carbon atoms, and arylcarbonyloxy groups having 6 to 30 carbon atoms, such as formyloxy, acetyloxy, pivaloyloxy, stearoyloxy, benzoyloxy, and phenylcarbonyloxy. Preferable examples of carbamoyloxy groups include carbamoyloxy groups having 1 to 30 carbon atoms, such as N,N-dimethylcarbamoyloxy, N,N-diethylcarbamoyloxy, morpholinocarbonyloxy, N,N-di-n-octylaminocarbonyloxy, and N-n-octylcarbamoyloxy. Preferable examples of alkoxycarbonyloxy groups are alkoxycarbonyloxy groups having 2 to 30 carbon atoms, such as methoxycarbonyloxy, ethoxycarbonyloxy, t-butoxycarbonyloxy, and n-octylcarbonyloxy.

Preferable examples of aryloxycarbonyloxy groups include aryloxycarbonyloxy groups having 7 to 30 carbon atoms, such as phenoxycarbonyloxy. Examples of alkylamino groups include alkylamino groups having 1 to 30 carbon atoms, such as methylamino and dimethylamino. Preferable examples of arylamino groups include arylamino groups having 6 to 30 carbon atoms, such as anilino and diphenylamino. Preferable examples of acylamino groups include formylamino groups, alkylcarbonylamino groups having 1 to 30 carbon atoms, and arylcarbonylamino groups having 6 to 30 carbon atoms, such as formylamino, acetylamino, pivaloylamino, lauroylamino, benzoylamino, and 3,4,5-tri-n-octyloxyphenylcarbonylamino. Preferable examples of aminocarbonylamino groups include aminocarbonylamino groups having 1 to 30 carbon atoms, such as carbamoylamino, N,N-dimethylaminocarbonylamino, N,N-diethylaminocarbonylamino, and morpholinocarbonylamino.

Preferable examples of alkoxycarbonylamino groups include alkoxycarbonylamino groups having 2 to 30 carbon atoms, such as methoxycarbonylamino, ethoxycarbonylamino, t-butoxycarbonylamino, and n-octadecyloxycarbonylamino. Preferable examples of aryloxycarbonylamino groups include aryloxycarbonylamino groups having 7 to 30 carbon atoms, such as phenoxycarbonylamino. Preferable examples of sulfamoylamino groups include sulfamoylamino groups having 0 to 30 carbon atoms, such as sulfamoylamino, N,N-dimethylaminosulfonylamino, and N-n-octylaminosulfonylamino. Preferable examples of alkyl- and arylsulfonylamino groups include alkylsulfonylamino groups having 1 to 30 carbon atoms and arylsulfonylamino groups having 6 to 30 carbon atoms, such as methylsulfonylamino, butylsulfonylamino, and phenylsulfonylamino. Preferable examples of alkylthio groups include alkylthio groups having 1 to 30 carbon atoms, such as methylthio, ethylthio, and n-hexadecylthio. Preferable examples of arylthio groups include arylthio groups having 6 to 30 carbon atoms, such as phenylthio. Preferable examples of heterocyclicthio groups are heterocyclicthio groups having 2 to 30 carbon atoms, such as 2-benzothiazolylthio and tetrazole-5-ylthio.

Preferable examples of sulfamoyl groups are substituted or unsubstituted sulfamoyl groups having 0 to 30 carbon atoms, such as N-ethylsulfamoyl, N-(3-dodecyloxypropyl)sulfamoyl, N,N-dimethylsulfamoyl, N-acetylsulfamoyl, N-benzoylsulfamoyl, and N—(N'phenylcarbamoyl)sulfamoyl. Preferable examples of alkylsulfinyl groups and arylsulfinyl groups include alkyl sulfinyl groups having 1 to 30 carbon atoms and arylsulfinyl groups having 6 to 30 carbon atoms, such as methylsulfinyl, ethylsulfinyl, and phenylsulfinyl. Preferable examples of alkyl- and arylsulfonyl groups include alkylsulfonyl groups having 1 to 30 carbon atoms, and arylsulfonyl groups having 6 to 30 carbon atoms, such as methylsulfonyl, ethylsulfonyl, and phenylsulfonyl. Preferable examples of acyl groups include formyl groups, alkylcarbonyl groups having 2 to 30 carbon atoms, arylcarbonyl groups having 7 to 30 carbon atoms, and heterocyclic carbonyl groups, having 4 to 30 carbon atoms, that are bonded to carbonyl groups, such as acetyl, pivaloyl, stearoyl, benzoyl, 2-pyridylcarbonyl, and 2-furylcarbonyl. Preferable examples of aryloxycarbonyl groups include aryloxycarbonyl groups having 7 to 30 carbon atoms, such as phenoxycarbonyl.

Preferable examples of alkoxycarbonyl groups include alkoxycarbonyl groups having 2 to 30 carbon atoms, such as methoxycarbonyl, ethoxycarbonyl, t-butoxycarbonyl, and n-octadecyloxycarbonyl. Preferable examples of carbamoyl groups include carbamoyl groups having 1 to 30 carbon atoms, such as carbamoyl, N-methylcarbamoyl, N,N-dimethylcarbamoyl, N,N-di-n-octylcarbamoyl, and N-(methylsulfonyl)carbamoyl. Preferable examples of arylazo groups and heterocyclic azo groups include arylazo groups having 6 to 30 carbon atoms and heterocyclic azo groups having 3 to 30 carbon atoms, such as phenylazo and 1,3,4-thiadiazole-2-ylazo. Preferable examples of imide groups include N-succinimide and N-phthalimide. Preferable examples of phosphino groups include phosphino groups having 2 to 30 carbon atoms, such as dimethylphosphino, diphenylphosphino, and methylphenoxyphosphino. Preferable examples of phosphinyl groups include phosphinyl groups having 2 to 30 carbon atoms, such as phosphinyl, dioctyloxyphosphinyl, and diethoxyphosphinyl. Preferable examples of phosphinyloxy groups include phosphinyloxy groups having 2 to 30 carbon atoms, such as diphenoxyphosphinyloxy and dioctyloxyphosphinyloxy. Preferable examples of phosphinylamino groups include phosphinylamino groups having 2 to 30 carbon atoms, such as dimethoxyphosphinylamino and dimethylaminophosphinylamino. Preferable examples of silyl groups include silyl groups having 3 to 30 carbon atoms, such as trimethylsilyl, t-butyldimethylsilyl, and phenyldimethylsilyl.

The above substituents may themselves be substituted with the above substituents. Examples of such substituents include arylalkyl groups, acylaminoaryloxy groups, alkylcarbonylaminosulfonyl groups, arylcarbonylaminosulfonyl groups, alkylsulfonylaminocarbonyl groups, and arylsulfonylaminocarbonyl group. Specific examples include methylsulfonylaminocarbonyl, p-methylphenylsulfonylaminocarbonyl, acetylaminosulfonyl, and benzoylaminosulfonyl.

The compound represented by general formula (I) will be described in detail below.

The compound represented by general formula (I) comprises three or more sulfonic acid groups. The three sulfonic acid groups are represented by the two instances of X in general formula (I) and by one or more sulfonic acid groups contained in one or more of the groups represented by $R^1$ to $R^8$. Acid groups such as the sulfonic acid groups may be in the form of groups forming salts through the dissociation of protons.

The compound represented by general formula (I) is characterized by having a substituent with the bulkiness of an ethyl group or greater on the polymethine group moieties represented by $L^1$ to $L^3$.

In general formula (I), each of $R^1$ and $R^2$ independently represents a substituent. These substituents can be selected from the above-described group of substituents. Each of $R^1$ and $R^2$ preferably represents a halogen atom, alkyl group (including a linear, branched, or cyclic alkyl group), aryl group, heterocyclic group, cyano group, carboxylic acid group, alkoxy group, aryloxy group, heterocyclic oxy group, amino groups (including an anilino group), acylamino group, aminocarbonylamino group, alkoxycarbonylamino group, aryloxycarbonylamino group, sulfamoylamino group, alkyl or arylsulfonylamino group, alkylthio group, arylthio group, heterocyclic thio group, sulfamoyl group, sulfonic acid group, alkyl or arylsulfonyl group, acyl group, alkoxycarbonyl group, carbamoyl group, or imide group. The substituent of more preference is a halogen atom, alkyl group (including a linear, branched, or cyclic alkyl group), aryl group, heterocyclic group, carboxylic acid group, alkoxy group, amino group (including an anilino group), acylamino group, sulfamoyl group, sulfonic acid group, carbamoyl group, or imide group. The substituent of even greater preference is a halogen atom, linear, branched, or cyclic alkyl group having 1 to 6 carbon atoms, aryl group having 6 to 10 carbon atoms, heterocyclic group having 1 to 10 carbon atoms, carboxylic acid group, or sulfonic acid group. The substituent of still greater preference is a bromine atom, iodine atom, methyl group, ethyl group, phenyl group, naphthyl group, thienyl group, furyl group, or pyridyl group.

In general formula (I), m and n represent integers of 0 to 3. When m and n represent 2 or 3, the multiple instances of $R^1$ and $R^2$ may be identical or different. It is preferable for m and n to represent 0 or 1, and preferably for them to represent 0.

In general formula (I), $R^3$ to $R^6$ may be identical or different. Each represents a substituted or unsubstituted alkyl group. This alkyl group is identically defined with the alkyl groups at $R^1$ and $R^2$; when it comprises a substituent, the substituent can be selected from the above-described group of substituents. Each of $R^3$ to $R^6$ preferably independently represents an alkyl group with 1 to 20 total carbon atoms, more preferably an alkyl group with 1 to 15 total carbon atoms, further preferably an alkyl group with 1 to 10 total carbon atoms, and still further preferably, an alkyl group with 1 to 3 total carbon atoms. Each of $R^3$ to $R^6$ preferably independently represents an unsubstituted alkyl group, with a methyl group being preferred.

In general formula (I), $R^7$ and $R^8$ may be identical or different; each represents a substituted or unsubstituted alkyl group. The alkyl group may be a linear alkyl group (preferably a linear alkyl group having 1 to 30 carbon atoms), a branched alkyl group (preferably a branched alkyl group having 3 to 30 carbon atoms), or a cyclic alkyl group (including an alkyl group having a tricyclic structure, preferably a cycloalkyl group having 3 to 30 carbon atoms or a bicyclic alkyl group having 5 to 30 carbon atoms (a monovalent group obtained by removing a single hydrogen atom from a bicycloalkane having 5 to 30 carbon atoms)). Examples include methyl, ethyl, n-propyl, isopropyl, t-butyl, n-octyl, eicosyl, 2-ethylhexyl, cyclohexyl, cyclopentyl, 4-n-dodecylcyclohexyl, bicyclo[1,2,2]heptane-2-yl, and bicyclo[2,2,2]octane-3-yl.

Of these, a linear alkyl group having 1 to 20 carbon atoms is preferable, a linear alkyl group having 1 to 10 carbon atoms, is more preferred, and a linear alkyl group having 1 to 5 carbon atoms is further more preferred.

The types, number, and positions of substituents on substituted alkyl groups represented by $R^7$ and $R^8$ are not specifically limited. When $R^7$ or $R^8$ is a substituted alkyl group, the substituent is preferably a halogen atom, carboxylic acid group, sulfonic acid group, phosphonic acid group, alkylthio group, arylthio group, or heterocyclic thio group; more preferably a carboxylic acid group, sulfonic acid group, or phosphonic acid group; and further preferably a sulfonic acid group. When the substituted alkyl group is a substituted linear alkyl group, the substitution site is preferably a site located two or more carbon atoms away from the nitrogen atom to which the substituted linear alkyl group substitutes as $R^7$ or $R^8$, and preferably the terminal carbon atom. The number of substituents is preferably 1.

Each of $L^1$ to $L^3$, which may be identical or different, represents a substituted or unsubstituted methine group. However, at least one from among $L^1$ to $L^3$ represents a methine group having a substituent with the bulkiness of an ethyl group or greater. r represents an integer of 0 to 3. When r is 2 or greater, the multiple instances of $L^2$ and $L^3$ may be identical or different. When $L^1$ to $L^3$ represent substituted methine groups, the substituents may be selected from the above-described group of substituents. When any two or more from among $L^1$ to $L^3$ represent substituted methine groups, the substituents may be bonded together to form a ring.

Specific examples of substituents having the bulkiness of an ethyl group or greater and specific examples of cases where the substituents bond together to form rings are given below. The examples given below show structures of the polymethine group moiety represented by $L^1$ to $L^3$ wherein r=2 and $L^3$ is sandwiched between two instances of $L^2$ and contains a substituent having the bulkiness of an ethyl group or greater. An "*" indicates a position bonding to one of the other two partial structures.

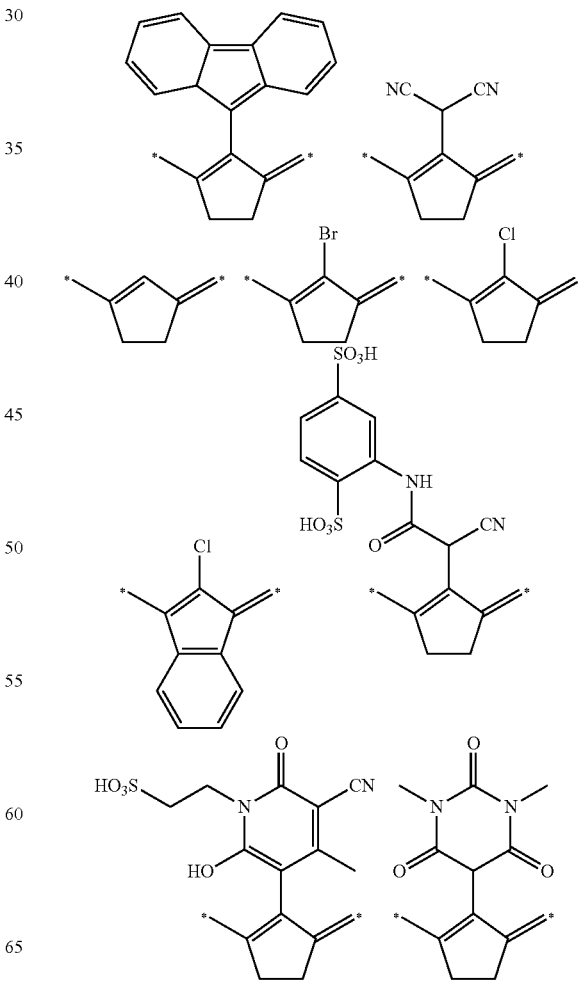

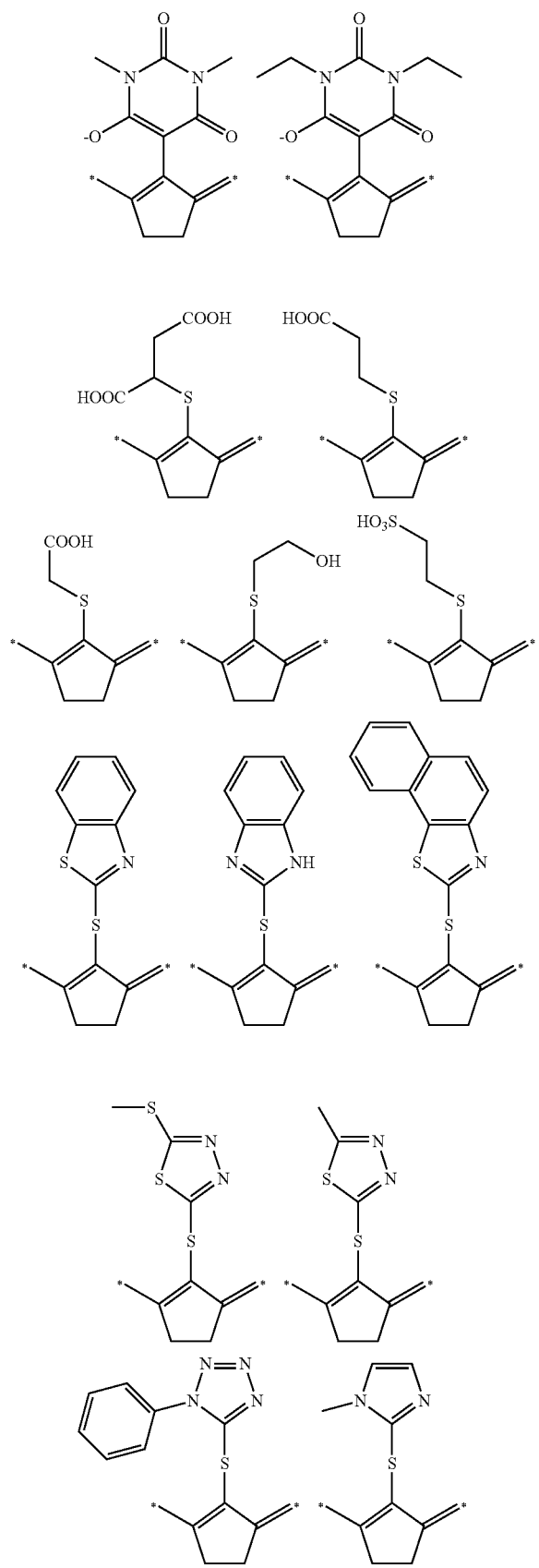
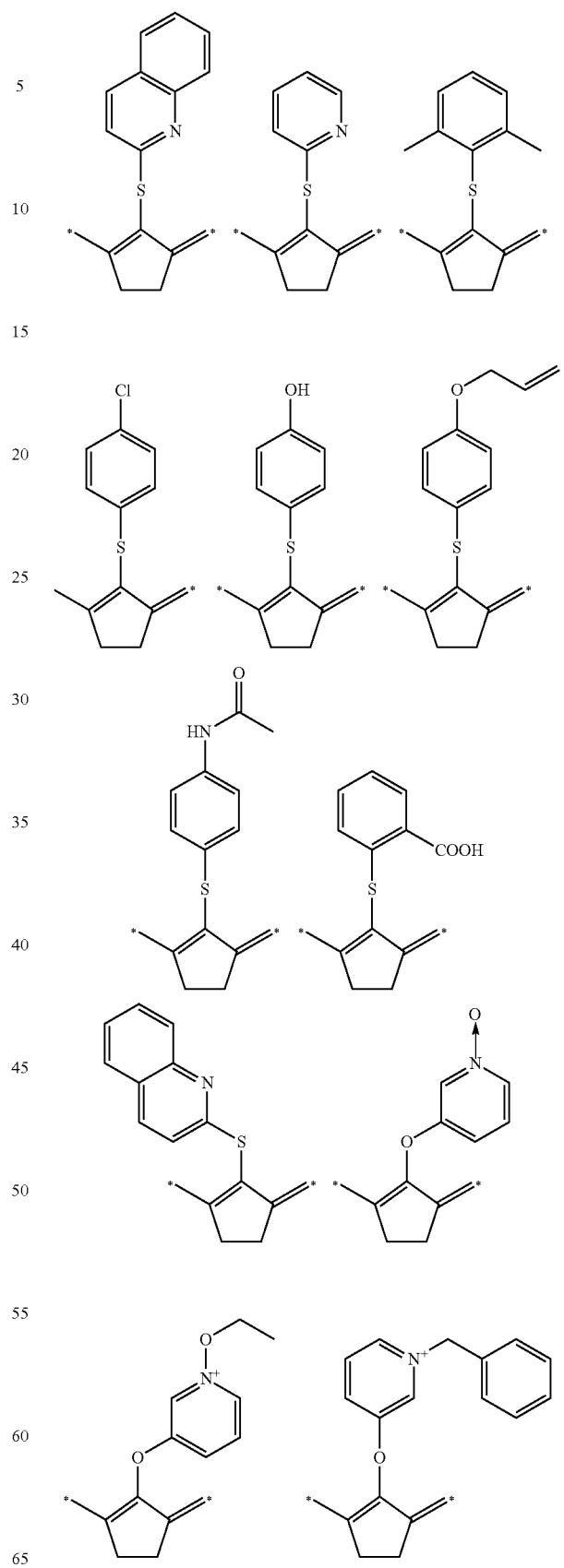

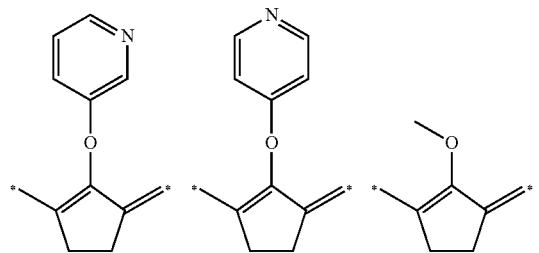
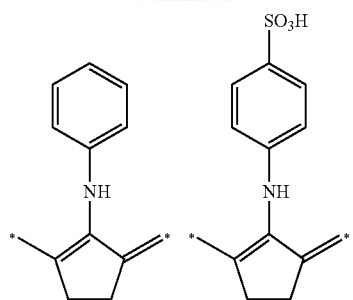
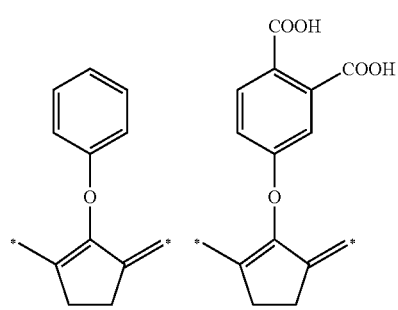
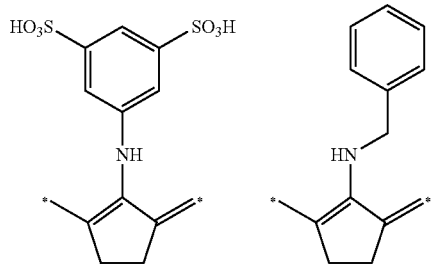
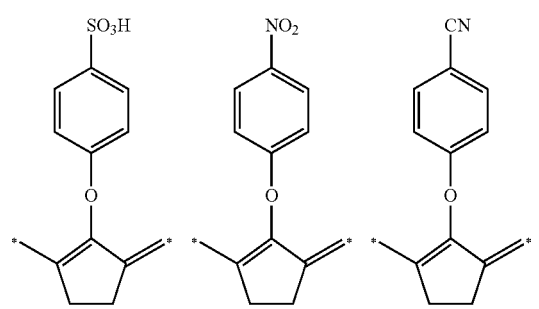
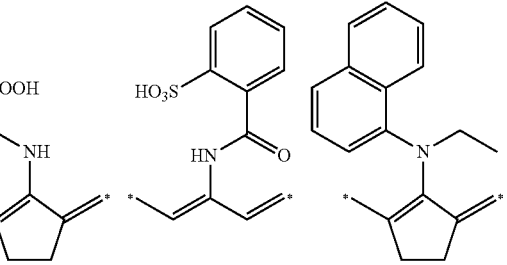
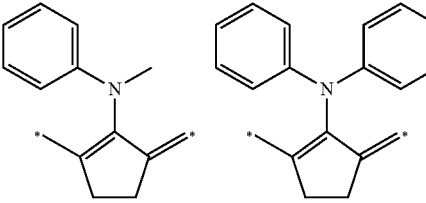
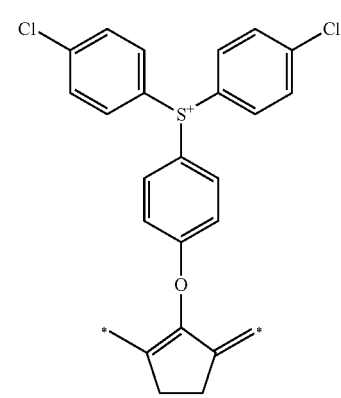
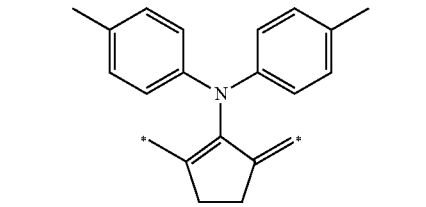
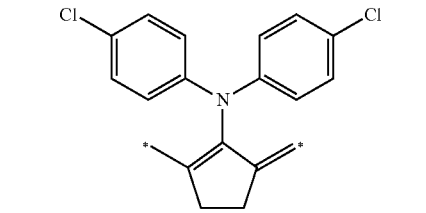
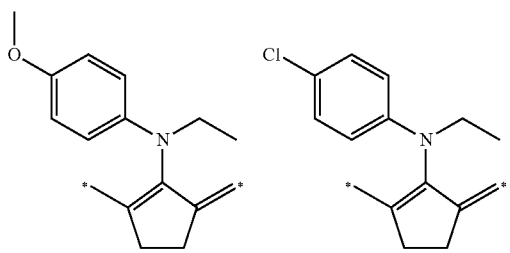
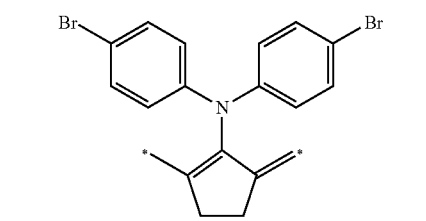

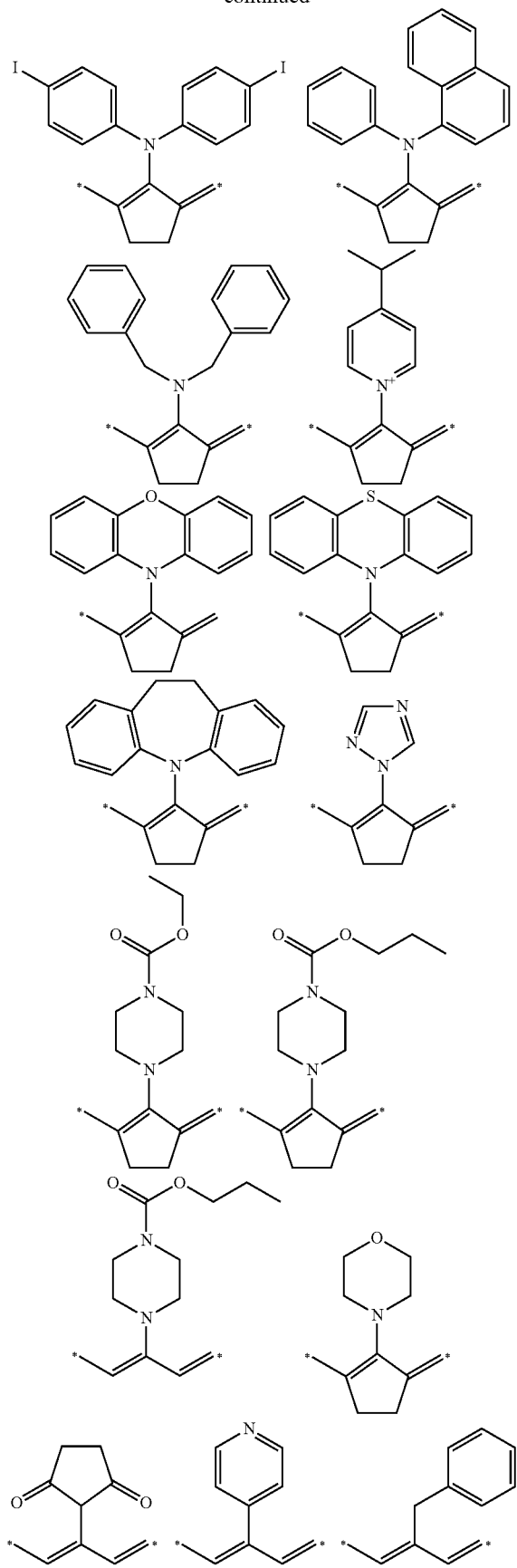
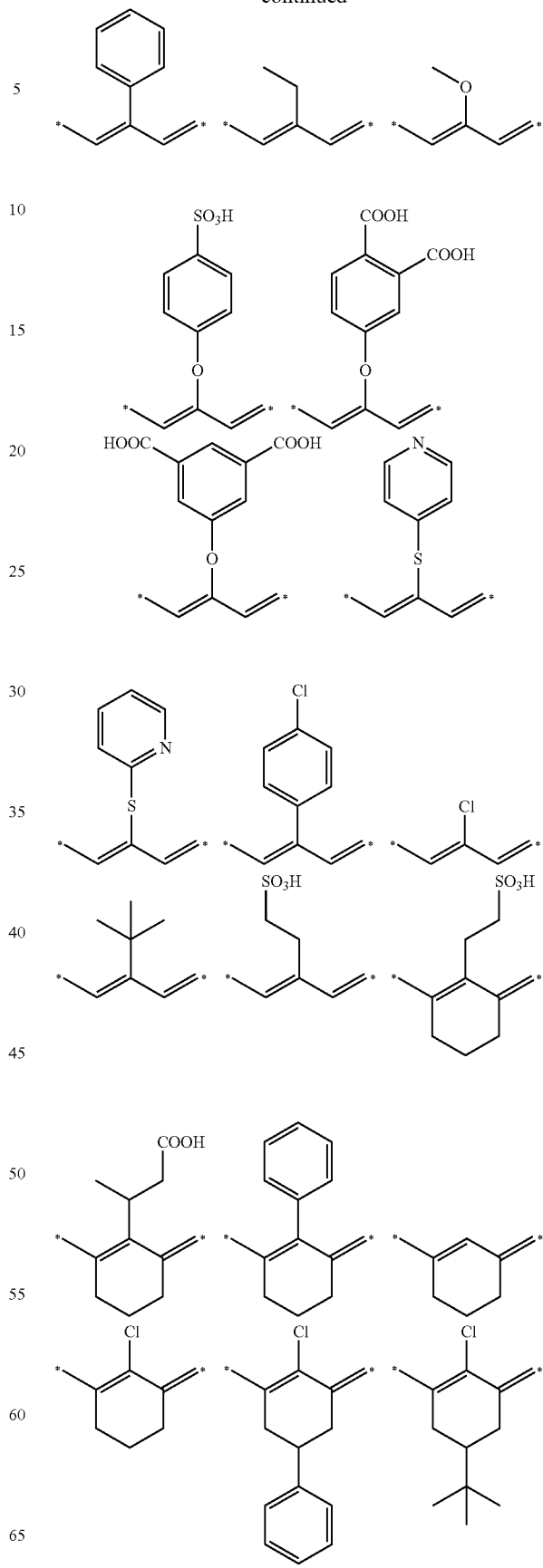

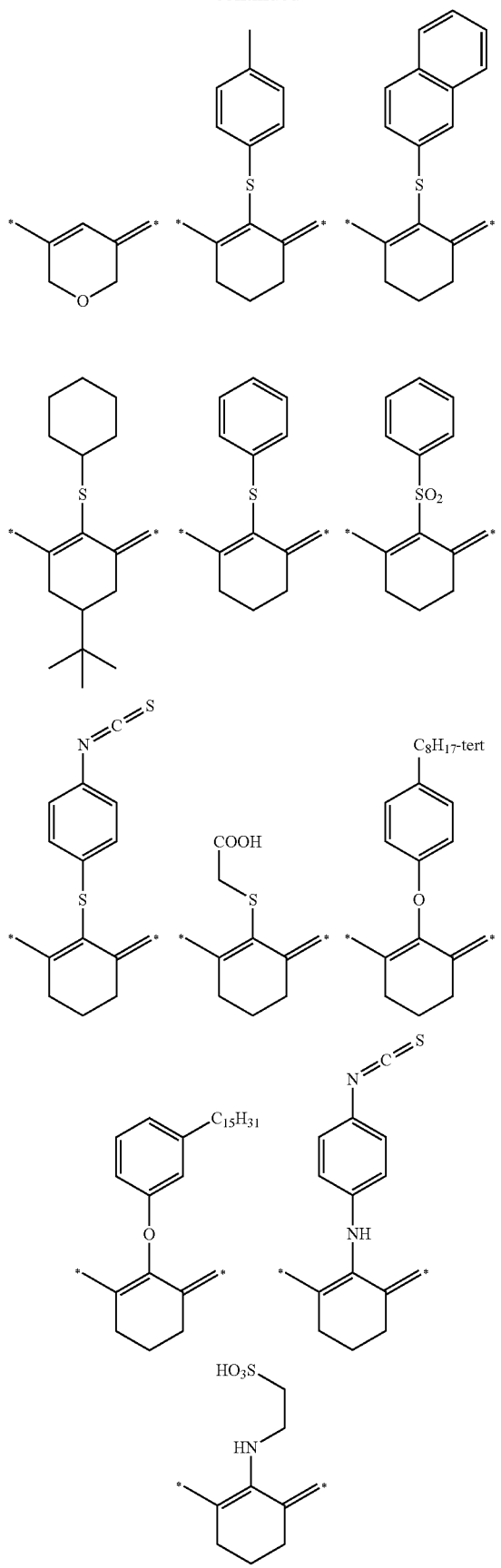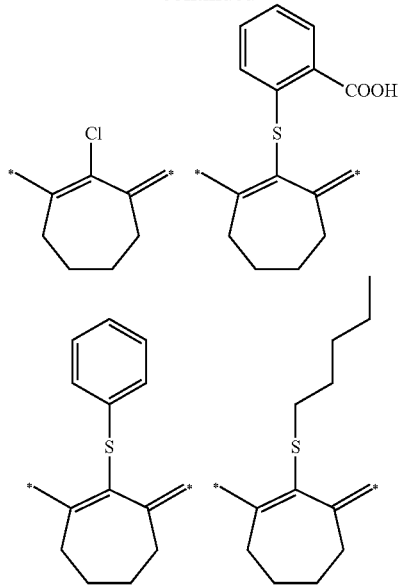

r represents an integer of 0 to 3, preferably 1 to 3, more preferably 2 to 3, and further preferably 3. At least one from among $L^1$ to $L^3$ preferably represents an unsubstituted methine group, more preferably 1 to 3 from among $L^1$ to $L^3$ represent substituted methine groups and the remainder represent unsubstituted methine groups, further preferably one represents a substituted methine group and the remainder represent unsubstituted methine groups.

When an acid group is in the form of group forming a salt, it preferably forms a salt with a negative charge, or a salt with an alkali metal or alkaline earth metal. Preferable alkali metals and alkaline earth metals are Na and K, with Na being more preferred.

The positive charge of the compound represented by general formula (I) is neutralized by a counter anion either inside or outside the molecule. Examples of such counter anions are: halogen ions such as chlorine ions, bromine ions, and iodine ions; carboxylate ions such as acetate ions, oxalate ions, fumarate ions, and benzoate ions; sulfonate ions such as p-toluene sulfonate, methane sulfonate, butane sulfonate, and benzene sulfonate; sulfuric acid ions; perchloric acid ions; carbonic acid ions; and nitric acid ions. When a group having a negative charge, such as a carboxylate group or sulfonate group, is present within the molecule, it may form an intramolecular salt with a positively charged compound. Preferable examples of extramolecular counter anions include halogen ions, methane sulfonate ions, and sulfuric acid ions. More preferred examples are chloro ions, bromo ions, and methane sulfonate ions.

The compound represented by general formula (I) preferably is the compound represented by general formula (II) above.

When $R^9$ in general formula (II) represents an alkyl group, the alkyl group preferably comprises a total of 2 to 20 carbon atoms, more preferably 2 to 15 carbon atoms, and further preferably, 2 to 10 carbon atoms. Specific preferred examples include an ethyl group, n-propyl group, 2-propyl group, and cyclopropyl group; examples of greater preference include an ethyl group, n-propyl group, 2-propyl group, and cyclopropyl group.

When $R^9$ represents an aryl group, the aryl group preferably comprises a total of 5 to 20 carbon atoms, preferably 5 to 15 carbon atoms, and more preferably, 5 to 10 carbon atoms. Specific preferred examples are a phenyl group, 4-methylphenyl group, 4-phenylphenyl group, and naphthyl group.

When $R^9$ represents an arylalkyl group, the arylalkyl group preferably comprises a total of 7 to 30 carbon atoms, more preferably 7 to 20 carbon atoms, and further preferably, 7 to 10 carbon atoms. Specific preferred examples include a benzyl group, phenylethyl group, and phenylpropyl group.

When $R^9$ represents a heterocyclic group, the heterocyclic group preferably comprises a total of 1 to 20 carbon atoms, more preferably 1 to 15 carbon atoms, and further preferably, 1 to 10 carbon atoms. Specific preferred examples include a 4-pyridyl group, 2-furyl group, 2-thienyl group, and 2-oxopyrrolidine-1-yl group.

When $R^9$ represents an acylamino group, the acylamino group preferably comprises a total of 1 to 20 carbon atoms, more preferably 1 to 15 carbon atoms, and further preferably, 1 to 10 carbon atoms. Specific preferred examples include an acetylamino group, benzoylamino group, pivaloylamino group, and 4-phenylbenzoylamino group.

When $R^9$ represents an arylamino group, the arylamino group preferably comprises a total of 1 to 20 carbon atoms, more preferably 1 to 15 carbon atoms, and further preferably, 1 to 10 carbon atoms. Specific preferred examples include an N-phenylamino group, N-tolylamino group, and N,N-diphenylamino group.

When $R^9$ represents an N-aryl-N-alkylamino group, the N-aryl-N-alkylamino group preferably comprises a total of 7 to 30 carbon atoms, more preferably 7 to 20 carbon atoms, and more preferably, 7 to 15 carbon atoms. Specific preferred examples include an N-phenyl-N-methylamino group and N-tolyl-N-methylamino group.

When $R^9$ represents an arylthio group, the arylthio group preferably comprises a total of 1 to 20 carbon atoms, more preferably 1 to 15 carbon atoms, and further preferably, 1 to 10 carbon atoms. Specific preferred examples include a phenylthio group, tolylthio group, 4-phenylphenylthio group, and naphthylthio group.

When $R^9$ represents an aryloxy group, the aryloxy group preferably comprises a total of 1 to 20 carbon atoms, more preferably 1 to 15 carbon atoms, and further preferably, 1 to 10 carbon atoms. Specific preferred examples include a phenyloxy group, 4-acetylaminophenyloxy group, 4-phenylphenyloxy group, and naphthyloxy group.

When $R^9$ represents an acylaminoaryloxy group, the acylaminoaryloxy group preferably comprises a total of 7 to 30 carbon atoms, more preferably 7 to 20 carbon atoms, and further preferably, 7 to 15 carbon atoms. A specific preferred example includes a benzoylaminophenyloxy group.

Each of $R^{10}$ and $R^{11}$ independently represents an alkyl group substituted with a carboxylic acid group, sulfonic acid group, or phosphonic acid group. In $R^{10}$ and $R^{11}$, which may be identical or different, it suffices for the alkyl group to be a linear alkyl group (preferably a linear alkyl group having 1 to 30 carbon atoms), branched alkyl group (a branched alkyl group having 3 to 30 carbon atoms), or a cyclic alkyl group (including one having a tricyclic structure, preferably a cycloalkyl group having 3 to 30 carbon atoms, or a bicyclic alkyl group having 5 to 30 carbon atoms (a monovalent group obtained by removing one hydrogen atom from a bicycloalkane having 5 to 30 carbon atoms)). Examples include methyl, ethyl, n-propyl, isopropyl, t-butyl, n-octyl, eicosyl, 2-ethylhexyl, cyclohexyl, cyclopentyl, 4-n-dodecylcyclohexyl, bicyclo[1,2,2]heptane-2-yl, and bicyclo[2,2,2]octane-3-yl. Of these, a linear alkyl group with 1 to 20 carbon atoms is preferable, a linear alkyl group with 1 to 10 carbon atoms is more preferred, and a linear alkyl group with 1 to 5 carbon atoms is further preferred.

In $R^{10}$ and $R^{11}$, neither the number nor position of the carboxylic acid group, sulfonic acid group, or phosphonic acid group is specifically limited. However, each of $R^{10}$ and $R^{11}$ preferably represents an alkyl group having carboxylic acid group or sulfonic acid group, and more preferably represents an alkyl groups having sulfonic acid groups. The sulfonic acid groups may form salts through the dissociation of hydrogen atoms.

When $R^{10}$ and $R^{11}$ are substituted with the above groups, the position of the substituent is preferably two or more carbon atoms away from the nitrogen atom to which each of $R^{10}$ and $R^{11}$ substitutes, preferably the terminal carbon atom.

It is particularly necessary for a fluorescence imaging agent for use within an organism to be water soluble. The water solubility of the near infrared fluorescence imaging agent of the present invention is markedly improved by incorporating three or more sulfonic acid groups into the above compound. To achieve good water solubility, the total number of sulfonic acid groups, carboxylic acid groups, and phosphonic acid groups is preferably four or more. To facilitate synthesis, the number of sulfonic acid groups, carboxylic acid groups, and phosphonic acid groups is 10 or fewer, preferably 8 or fewer. The improvement in water solubility can be checked by measuring the partition coefficient of the individual compound. For example, the partition coefficient can be checked by measurement in a butanol/water two-phase system. More specifically, the incorporation of three or more sulfonic acid groups yields an n-butanol/water partition coefficient log Po/w of −1.00 or lower.

Water solubility within an organism can be determined based on an index of whether or not the compound settles out or precipitates over time at 36° C. when dissolved in physiological saline.

The substance contained as an imaging component in the near infrared fluorescence imaging agent of the present invention is not limited other than that it be the compound represented by general formula (I) or a pharmacologically acceptable salt thereof. Such compounds can be synthesized by the known manufacturing methods for cyanine dye compounds disclosed in "Cyanine Dyes and Related Compounds," F. M. Hamer, John Wiley and Sons, New York, 1964; Cytometry, 10, 3-10 (1989); Cytometry, 11, 418-430 (1990); Cytometry, 12, 723-730 (1990); Bioconjugate Chem. 4, 105-111 (1993), Anal. Biochem., 217, 197-204 (1994); Tetrahedron, 45, 4845-4866 (1989); EP-A-0591820A1; EP-A-0580145A1; and the like. Alternatively, they can be semisynthesized by known methods from commercial cyanine dye compounds. In particular, they can be synthesized by reacting a dianil compound with a heterocyclic compound quaternary salt.

Specific examples of the present invention are given below.

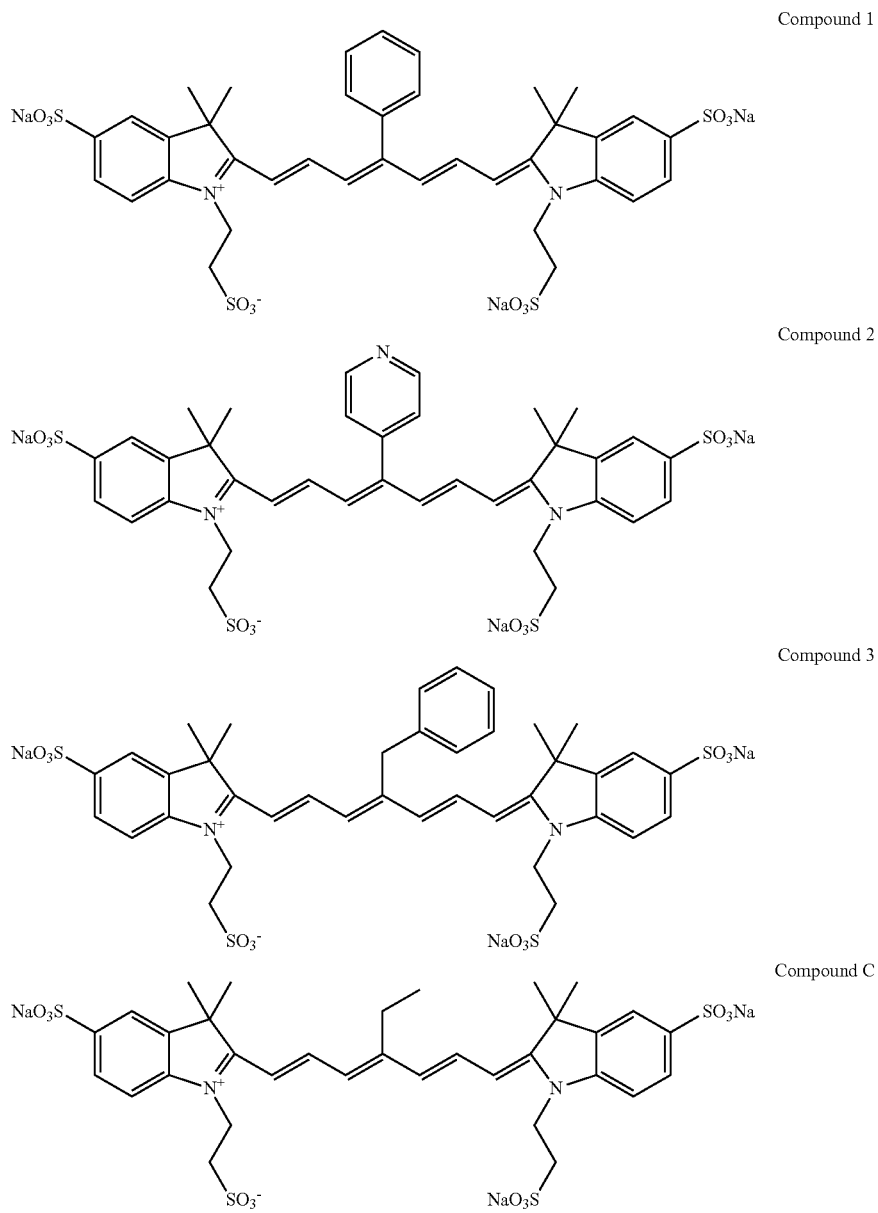

Compound 1

Compound 2

Compound 3

Compound C

The above compounds exhibit absorption and fluorescence in the near infrared light region of 700 to 1,300 nm, particularly about 700 to 900 nm, and have a molar absorption coefficient of 100,000 or greater.

The near infrared fluorescence imaging agent of the present invention is not specifically limited other than that it comprise the compound represented by general formula (I) and/or a pharmacologically acceptable salt thereof. The compound or salt thereof may be employed singly or in combination in the imaging agent.

Specifically, the imaging agent contains the above compound or a pharmacologically acceptable salt thereof, or the above compound suspended or dissolved in a solvent such as injection-use distilled water, physiological saline, or Ringer's solution. As needed, pharmacologically acceptable additives, such as a support or an excipient, can be added. Examples of these additives include pharmacologically acceptable electrolytes, buffers, substances such as cleansing agents, and substances that enhance stability and solubility by adjusting the osmotic pressure (such as cyclodextrin and ribosomes). Various additives generally employed in related fields can be employed. The near infrared fluorescence imaging agent of the present invention is preferably manufactured for pharmacological use by means of a sterile process.

The imaging agent can be administered to an organism by injection, by spraying, by coating, by intravascular administration (veins, arteries), oral administration, intraperitoneal administration, transdermal administration, subdermal administration, intravesical administration, or intrabronchial administration. The present imaging agent is preferably administered in the form of an aqueous agent, emulsion, or suspension into a blood vessel.

The dose of the near infrared fluorescence imaging agent of the present invention that is employed is not specifically limited other than that the dose employed permit detection of the site to be finally diagnosed, and is suitably adjusted based on the type of compound releasing the near infrared light that is employed, or age, weight, target organ of administration, and the like. Typically, the dose is 0.01 to 100 mg/kg of body weight, preferably 0.01 to 20 mg/kg of body weight, based on the quantity of compound. The imaging agent of the present invention can be suitably employed in various animals in addition to humans. The form, route, and dose administered are suitably determined based on the body weight and conditions of the subject animal.

The compound represented by general formula (I), and, preferably, the compound represented by general formula (II), have a marked tendency to accumulate in tumor tissue. Utilizing this characteristic, it is possible to use the fluorescence imaging agent of the present invention to specifically image tumor tissue. Further, the compound of the present invention has a long half-life in serum, making it possible to anticipate good functioning as a blood vessel imaging agent, as well.

The near infrared fluorescence imaging agent of the present invention can be employed in fluorescence imaging. This method is implemented by a known method. Various parameters such as the excitation wavelength and fluorescence wavelength to be detected are suitably determined to permit optimal imaging and evaluation based on the type of near infrared fluorescence imaging agent being administered and the subject of administration. The time required from when the near infrared fluorescence imaging agent of the present invention is administered to the measurement subject to when measurement by the fluorescence imaging method of the present invention begins varies depending on the type of the near infrared fluorescence imaging agent employed and the subject of administration. For example, when the compound represented by general formula (I) is incorporated into an imaging agent for the purpose of tumor imaging, the time elapsing after administration is considered to be about 4 to 120 hours. In particular, in the case of the compound represented by general formula (II), the time elapsing after administration is considered to be about 24 to 120 hours. When the time elapsed is too short, the fluorescence is excessively strong, making it impossible to clearly distinguish between the target site and other sites. When excessively long, the imaging agent is sometimes discharged from the body.

Research by the present inventors based on SF-64 revealed for the first time that cyanine compounds form complexes with albumin in plasma, thereby accumulating in tumors. The compound represented by general formula (I) having a substituent with the bulkiness of an ethyl group or greater in the polymethine moiety represented by $L^1$ to $L^3$ has a higher ability to bind albumin than SF-64.

Due to the high ability to bind albumin of the compound of the present invention, it can bind to albumin-binding proteins such as SPARC, cubilin, and TGF-beta. Thus, the compound of the present invention can be employed as an imaging agent in the course of imaging disease in which albumin-binding proteins play primary roles and are expressed in greater amounts than in normal tissue. The albumin-binding protein is preferably selected from among SPARC, cubilin, and TGF-beta, and is preferably SPARC.

The compound of the present invention or a pharmacologically acceptable salt thereof thus functions as a detecting agent for SPARC-expressing tissue and can be employed as a diagnostic drug for all pathology relating to SPARC. The pathology for which the compound of the present invention can be employed as an imaging agent includes abnormal reproductive states, tissue reconstruction, overformation, and excessive wound healing in any physical tissue including soft tissue, connective tissue, bone, solid organs, and blood vessels. Specific examples include cancer, diabetes and related retinal disorders, inflammation, arthritis, restenosis in blood vessel, sections of artificial vascular transplants, and intravascular devices.

The types of tumors that are detected by the compound of the present invention are those that are generally observed in mammals, including humans. These tumors can be generated by inoculation of test animals and the like. The tumors are also known as "neoplasmas," and come in many types and forms. The tumors to which the compound of the present invention is applied as an imaging agent are not limited, and may be any specific type or form of tumor. The compound of the present invention is useful for imaging tumor cells, related interstitial cells, solid tumors, and tumors relating to soft tissue, such as human soft tissue sarcomas. The tumor or cancer can be located in the mouth cavity, pharynx, digestive organs, respiratory organs, bones, joints (such as bone metastasis), soft tissue, skin (such as melanoma), breasts, genitalia, urinary system, eyes, eyeball sockets, brain, central nervous system (such as gliomas), or the endocrine system (such as the thyroid gland), and are not limited to primary tumors or cancers. Examples of tissues relating to the mouth cavity include tongue and mouth tissues. Cancers can occur in digestive system tissue, including the esophagus, stomach, duodenum, small intestine, colon, rectum, anus, liver, gall bladder, and pancreas. Respiratory cancers can occur in the pharynx, lungs, and bronchia. Tumors can occur in the cervix, uterus, ovaries, vulva, vagina, prostate, testicles, and penis, constituting the male and female genitalia, as well as in the bladder, kidneys, renal pelvis, and urethra, constituting the urinary system. Tumors and cancers can occur in the head and/or cervix. Tumors and cancers can also occur within the lymph tissue system. Examples thereof include Hodgkin's disease and non-Hodgkin's lymphomas. Tumors and cancers can occur in the hematogenic system. Examples thereof include multiple myeloma and leukemia, such as acute lympholeukemia, chronic lymphocytic leukemia, acute myelitic leukemia, and chronic myelitic leukemia. The tumor is preferably positioned in the bladder, liver, pancreas, ovaries, kidneys, esophagus, stomach, intestines, brain, skin, or breasts.

Albumin has affinity for SPARC. Accordingly, the compound of the present invention accumulates at lesion area expressing SPARC while accumulating little or not at all in healthy tissue.

The expression of SPARC protein in samples can be detected and quantified by any suitable method that is known in the field. Examples of suitable methods for detecting and quantifying proteins are the western blot method, enzyme-linked immunosorbent assay (ELISA), silver dye method, BCA assay (described in Smith et al., Anal. Biochem., 150, 76-85 (1985)), the Lowry protein assay, which is a form of protein-copper complex-based colorimetric analysis (described, for example, in Lowry et al., J. Biol. Chem., 193, 265-275 (1951)), and Bradford protein analysis based on the absorbance change of Coomassie blue G-250 in the course of protein binding (described, for example, in Bradford et al., Anal. Biochem., 72, 248 1976)). Tumor biopsies can be conducted by any conventional method, or conducted immunohistologically using anti-SPARC antibody (either monoclonal or polyclonal) in combination with a suitable visualization system (that is, HRP substrate and HRP-coupled secondary antibodies).

EXAMPLES

The present invention will be described more specifically below through examples. However, the scope of the present invention is not limited to the examples set forth below. The compound numbers given in the examples below correspond to the above-described compound examples. The names of the compounds indicated in the embodiments below do not necessarily conform to IUPAC naming conventions.

In the examples below, the serial numbers of the compounds and the compound structures correspond to the numbers of the compounds given by way of example above.

Intermediates for synthesizing the compound of the present invention were obtained by the following procedure.

5-Sulfo-2,3,3-trimethylindoleine was synthesized by a known synthesis method (Japanese Unexamined Patent Publication (KOKAI) Heisei No. 2-233658).

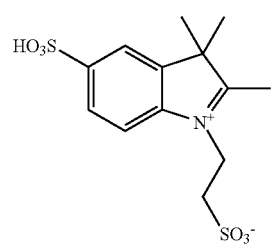

Intermediate 1

Intermediate 1 (a heterocyclic quaternary salt compound) was synthesized by a method described in the patent literature (Published Japanese Translation (TOKUHYO) No. 2002-526458 of a PCT International Publication (WO00/16810)).

That is, 2-chloroethanesulfononyl chloride was added dropwise over two hours while stirring at room temperature to 5-sulfo-2,3,3-trimethylindoleine dissolved in DMAC, then the mixture was stirred for another three hours. Methanol was added dropwise over 30 minutes, then an aqueous sodium hydroxide solution was added dropwise over one hour and stirred for another hour at room temperature. When the reaction was completed, acetonitrile was added dropwise over two hours and the mixture was left standing overnight at room temperature to allow crystals to precipitate. The crystals were collected by filtration, washed with a DMAc/methanol/water/acetonitrile=5/4/4/40 solution followed by acetonitrile, and dried under reduced pressure to obtain intermediate 1.

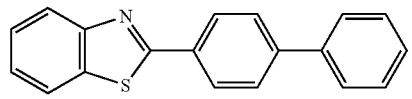

Intermediate 15

3-Phenylpyridine (1 equivalent) and 2 chlorobenzothiazole (2 equivalents) were stirred in DMAc at 100° C. for three hours. When the reaction was completed, acetone was added. The solid was collected by filtration, yielding intermediate 15.

The dianil compounds indicated below were obtained or synthesized by the method described in the patent literature (Published Japanese Translation (TOKUHYO) No. 2008-526802 of a PCT International Publication (WO2006/072580)).

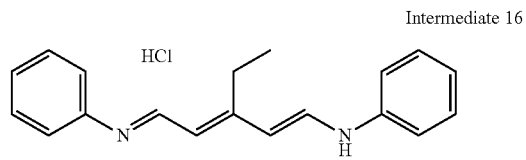 [SMILES: CCC(/C=C/Nc1ccccc1)=C\C=N\c1ccccc1 ; Cl]

Intermediate 16

1,7-Diazadiphenyl-3-ethyl-1,3,5-heptatriene monohydrochloride

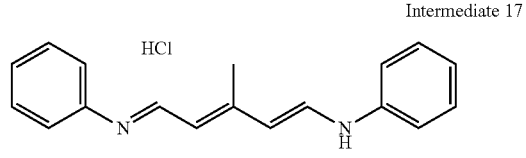 [SMILES: CC(/C=C/Nc1ccccc1)=C\C=N\c1ccccc1 ; Cl]

Intermediate 17

1,7-Diazadiphenyl-3-methyl-1,3,5-heptatriene monohydrochloride

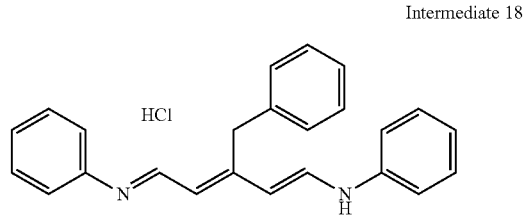 [SMILES: C(=C/C(=C/C=N/c1ccccc1)Cc1ccccc1)\Nc1ccccc1 ; Cl]

Intermediate 18

1,7-Diazadiphenyl-3-benzyl-1,3,5-heptatriene monohydrochloride

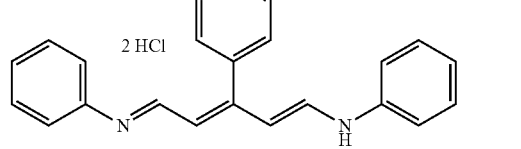

Intermediate 19

1,7-Diazadiphenyl-3-(4-pyridinyl)-1,3,5-heptatriene monohydrochloride

The compounds and salts thereof indicated below were manufactured by the methods indicated below, for example, using the above heteroquaternary salt compounds and dianil compounds or benzthiazole compounds.

A known heteroquaternary compound (5 mmoles), or one synthesized by a known method or the above-described synthesis method, and a known dianil compound (10 mmol), or one synthesized by a known method or the above-described synthesis method, or a benzthiazole compound (10 mmoles), is stirred for four hours at room temperature in a methanol solution in the presence of triethylamine (25 mmol) and acetic anhydride (45 mmol). To the reaction mixture is added sodium acetate (33 mmol) and the mixture is stirred for 30 minutes at room temperature. The crystals generated are removed by filtration and washed with methanol. When the presence of products other than the target compound is observed by reverse-phase thin layer chromatography, purification is conducted by size exclusion chromatography with methanol as the developing solvent or by reverse phase chromatography with a water/methanol mixed solvent as the developing solvent.

Compound 1: Synthesized by the above synthesis method using intermediates 1 and 15.

1H NMR (400 MHz, $D_2O$) δ 1.17 (s, 12H), 3.32 (t, 4H), 4.39 (t, 4H), 6.36 (d, 2H), 6.78 (d, 2H), 6.92-7.00 (m, 2H), 7.18-7.24 (m, 2H), 7.26-7.37 (m, 2H), 7.52-7.62 (m, 3H), 7.65-7.70 (m, 4H), MS(ESI+) 758 [M+1]+, λ max=750 nm Compound 2: Synthesized by the above synthesis method using intermediates 1 and 19.

1H NMR (400 MHz, $D_2O$) δ 1.29 (s, 12H), 3.36 (t, 4H), 4.45 (t, 4H), 6.44 (d, 2H), 6.81 (d, 2H), 7.20-7.35 (m, 6H), 7.74-7.78 (m, 4H), 8.76 (d, 2H), λ max=790 nm Compound 3: Synthesized by the above synthesis method using intermediates 1 and 18.

1H NMR (400 MHz, $D_2O$) δ 1.50 (s, 12H), 3.32 (t, 4H), 4.24 (s, 2H), 4.36 (t, 4H), 6.32 (d, 2H), 6.72 (d, 2H), 7.31 (d, 2H), 7.37-7.44 (m, 5H), 7.75-7.81 (m, 4H), 8.00 (dd, 2H), λ max=791 nm

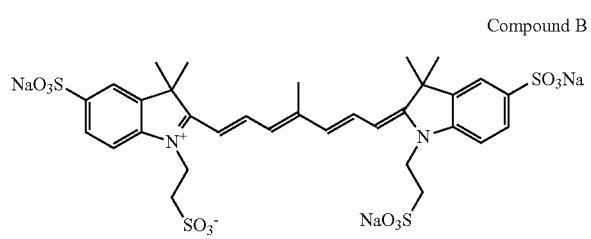

Compound B

Compound B (SF-64) was synthesized from intermediates 1 and 17 as described in paragraph [0058] of Japanese Patent 3,507,060.

Compound C was synthesized from intermediates 1 and 16 as described in paragraph [0058] of Japanese Patent 3,507,060.

Test Example 1

Serum Protein Binding Rate Test by Ultracentrifugation

The test substance was dissolved to 5 μg/mL in calf serum, vibrated for 20 minutes at 37° C., and subjected to density gradient centrifugation (1,000,000×g, 24 h) using NaBr. Following the centrifugation, the dye concentrations in the albumin fraction, lipoprotein fraction, and the remaining fractions were quantified by HPLC. The results are given in Table 1.

TABLE 1

| Compound | Level | Protein binding rate (%) | | |
|---|---|---|---|---|
| | | Albumin | lipoprotein | other |
| Compound B | Comparative Example | 60 | 1 | 39 |
| ICG | Comparative Example | 18 | 81 | 1 |
| Compound 1 | Invention | 65 | 1 | 34 |
| Compound 2 | Invention | 64 | 2 | 34 |
| Compound 3 | Invention | 70 | 2 | 28 |
| Compound C | Invention | 62 | 5 | 33 |

From Table 1, it is clear that the compounds of the present invention having the structure shown in general formula (I) exhibited a high binding rate for albumin in particular among the protein components present in serum. It is also clear that compounds with poor water solubility, such as ICG, bonded to lipoprotein among the protein components in serum.

Additionally, Table 1 clearly shows that as the bulkiness of the substituent on the methine chain increased, the albumin binding rate increased. Thus, it will be understood that the albumin binding property can be controlled by means of the bulkiness of the substituent on the methine chain.

Test Example 2

Intravenous Administration of Compounds to Mice, Plasma Sampling, and Evaluation of Half-Life in Plasma BALB-cA Jcl-nu/nu mice (CLEA Japan, Inc.) were purchased at eight weeks and reared in quarantine for about a week. The intravenous administration was conducted by dissolving the test substance to 1 mg/mL in physiological saline (Pharmacopoeia Japonica, Otsuka Pharmaceutical Factory, Inc.), employing a dose of 5 mL/kg, and employing a wing-shaped injection needle (27 G) to inject a single administration into a tail vein. Blood was collected at 5, 15, and 30 minutes, and 1, 2, 4, and 6 hours following administration. The blood was collected from the jugular vein with weak anesthetization. A quantity of about 50 μL was drawn each time. When blood collection was completed, the animals were euthanized by deep ether anesthetization. The collected blood samples were collected in heparin-treated syringes and transferred to centrifuging tubes. They were then cooled with ice and centrifugally separated (about 4° C., 8,200 g, 5 minutes) to obtain plasma (20 μL). To the plasma was added 40 μL of phosphate buffer and the mixture was stored temporarily in a freezer at −80° C. The test substance was tested in three male mice for each time period. The concentration of the test substance in samples obtained at the various times was calculated from a calibration curve after measuring the fluorescence intensity with an EnVision (GE Corp.). The half-life in plasma was the time required for the initial value of the concentration of the compound in the plasma to diminish by half. Conventionally, it is determined by measuring the concentration of the compound in the plasma samples as set forth above following intravenous administration of the test compound. The half-life in plasma is evaluated from a semilogarithmic plot of the logarithm of the concentration in plasma against the sample collection time. The apparent primary dissipation rate constant is equal to the slope of the line. The half life is the inverse of the dissipation rate constant (Gibaldi, M and Perrier, D, 1975, Pharmacokinetics, Marcel Dekker, New York).

The results of measurement of the half-lives in plasma of compound 1 and compound B and comparison of their murine plasma binding rates are given in Table 2.

TABLE 2

| | Compound | Half-life in plasma | Clearance in blood |
|---|---|---|---|
| Invention | Compound 1 | 0.31 h | 4.19 ml/min/Kg |
| Comparative Example | Compound B | 0.25 h | 10.2 ml/min/Kg |

From Table 2, it can be understood that the time transition of the blood concentration of albumin-binding compound 1 prepared according to the present invention was better than that of compound B. That is, the compound of the present invention, with a higher albumin-binding rate than SF-64, had an improved time for outlining a tumor compared to SF-64.

Text Example 3

Imaging Experiment

Suspensions of the human carcinoma cells HCT116 (SPARC expression +), A431 (SPARC expression −), and HT1080 (SPARC expression −) in physiological saline were injected subcutaneously into the right chest of BALB-cA Jcl-nu/nu mice (five weeks, CLEA Japan, Inc.). After 14 days, when the tumors had grown, the mice were employed in the experiment. Each test compound was dissolved in physiological saline to 0.5 mg/mL and administered in a single dose of 0.5 mg/kg to the tail veins of the mice. Following administration, imaging was conducted in LAS-4000 IR multicolor (Fuji Film) under weak anesthetization. Excitation light in the form of an IR LED (center wavelength 710 nm) and an excitation light-cutting filter in the form of an IR-use IR785 were employed in this process. The imaging times were 10 minutes, 30 minutes, and 1, 2, 4, 6, and 24 hours after administration. Each test compound was tested on three mice for each of the cell inoculations.

According to the method described in test example 3, compound (B) (black circles in the figure), compound 1 (squares), and compound 3 (triangles) were administered to mice inoculated with HCT116 cells. The transition over time of the ratio of the fluorescence intensity of the tumor site divided by the fluorescent intensity of the thigh site (S/N ratio) at various points in time was measured. The results are given in FIG. 1. Each test compound was tested on three mice for each of the cell inoculations.

From Table 2 and FIG. 1, it can be understood that compounds 1 and 3, which had high plasma protein-binding rates, maintained a high state of fluorescence ratio (S/N) of the tumor tissue (S: signal) to the normal tissue (for example, the thigh: N: noise) for a longer period than comparative compound B.

It is clear from the above results that the compound of the present invention had a higher plasma protein-binding rate than conventional compounds, and was thus able to maintain a good S/N ratio for an extended period.

Compound 1 of the present invention was administered to mice inoculated with various tumor cells and imaging was conducted according to the method described in test example 3. The imaging results at hours 2, 4, and 6 following administration are shown in FIG. 2.

Figure 2:
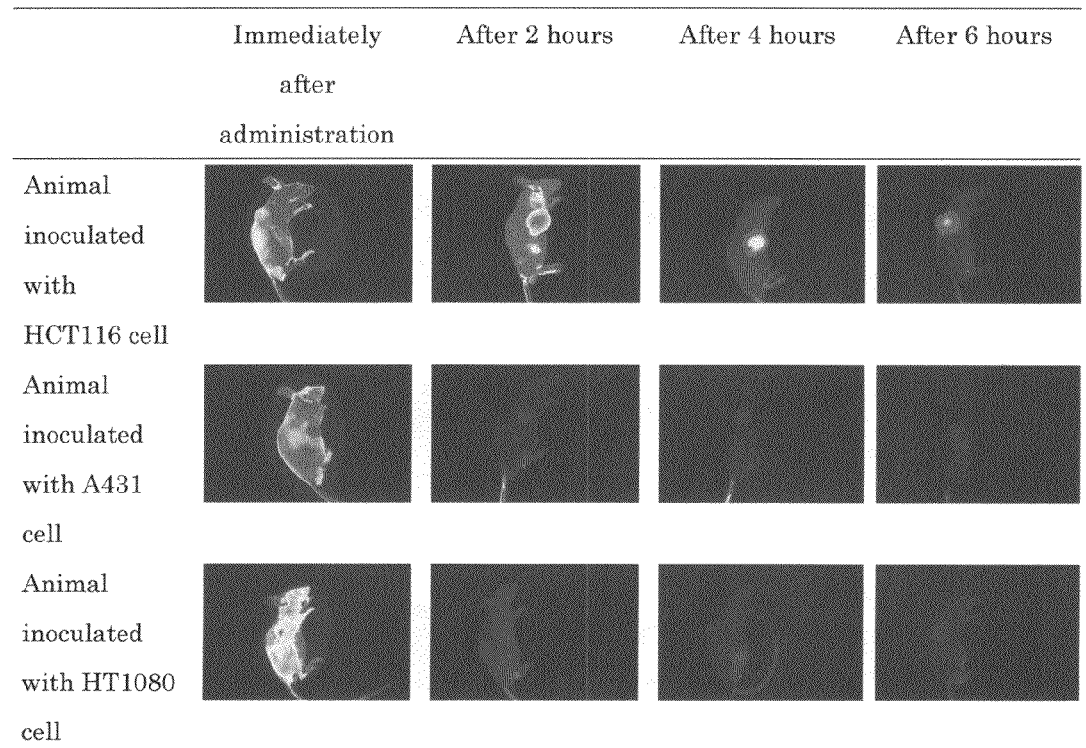
FIG. 2 shows pictures showing the imaging results immediately following administration, at two hours, at four hours, and at six hours when compound 1 of the present invention was administered to mice inoculated with various cancer cells.

From FIG. 2, it can be understood that compound 1 accumulated in cancer formed by inoculation of HCT116 cells, but compound 1 did not accumulate in cancers formed by inoculation with A431 cells or HT1080 cells. This confirmed the marked imaging effect on cancers expressing a high level of SPARC of the compound of the present invention.

Test Example 4

Analysis of Western Blot

The tumors of the mice used in imaging were extracted, rapidly frozen with liquid nitrogen, and pulverized with a CryoPress (Microtec Nichion). The tumor powder obtained was added to a cell lysate buffer (Cell Signaling Technology) and left for five minutes following ultrasonic treatment for one minute at 0° C. The dispersion was centrifuged at A 14,000 g for 10 minutes and the supernatant was removed. The quantity of protein in the supernatant was quantified with BCA protein assay (Piers Biotechnology). Solutions prepared by dilution with PBS were placed on a 12.5 percent polyacrylamide gel to 100 µg/well (Real Gel Plate, Biocraft) and analyzed by SDS gel electrophoresis on 12.5% polyacrylamide gel (REAL GEL PLATE, BIO CRAFT). Subsequently, Trans-Blot semi-dry cells (Bio-Rad) were employed to prepare electroblots on PVDF membrane and blocking was conducted for 12 hours with TPBS buffer containing 3 percent skim milk. Anti-SPARC antibody (SPARC (H-90) Santa Cruz) was bound as a primary antibody, anti-rabbit-IgG horse radish peroxidase-linked whole antibody from donkey (GE Healthcare) was bound as a secondary antibody, and intensified chemical luminescence detection was conducted with ECL plus (GE Healthcare). A fluorescence image reader (LAS-3000, Fuji Film) was employed for visualization.

The protein extracted from the tumor tissue of mice that had been employed in the imaging experiment shown in FIG. 2 was placed on SDS-PAGE and the gel was electroplotted on a PVDF membrane. Anti-SPARC antibody (SPARC (H-90)) was bound as the primary antibody and HRP-binding donkey anti-rabbit antibody was bound as the secondary antibody. Coloration was generated with ECL plus and images were picked up with a fluorescence imager. The results of tests conducted with proteins extracted from the tumor sites of animals inoculated with various tumor cells are given in FIG. 3: from the left, HCT116 (animal 1), HCT116 (animal 2), HCT116 (animal 3), HT1080 (animal 4), HT1080 (animal 5), HT1080 (animal 6), A431 (animal 7), A431 (animal 8), and A431 (animal 9).

Following an imaging experiment with mice in which tumors had been formed by inoculation with HCT116 cells according to the method described in test example 3, protein extracted from tumor and thigh tissue of the same mice was placed on SDS-PAGE and the gel was electroplotted on a PVDF membrane. Anti-SPARC antibody (SPARC (H-90)) was bound as the primary antibody and HRP-binding donkey anti-rabbit antibody was bound as the secondary antibody. Coloration was generated with ECL plus and images were picked up with a fluorescence imager. The results are given in FIG. 4: from the left, standard specimen (human SPARC), thigh extraction (animal 10), thigh extraction (animal 11), thigh extraction (animal 12), tumor extraction (animal 10), tumor extraction (animal 11), and tumor extraction (animal 12).

Figure 3:
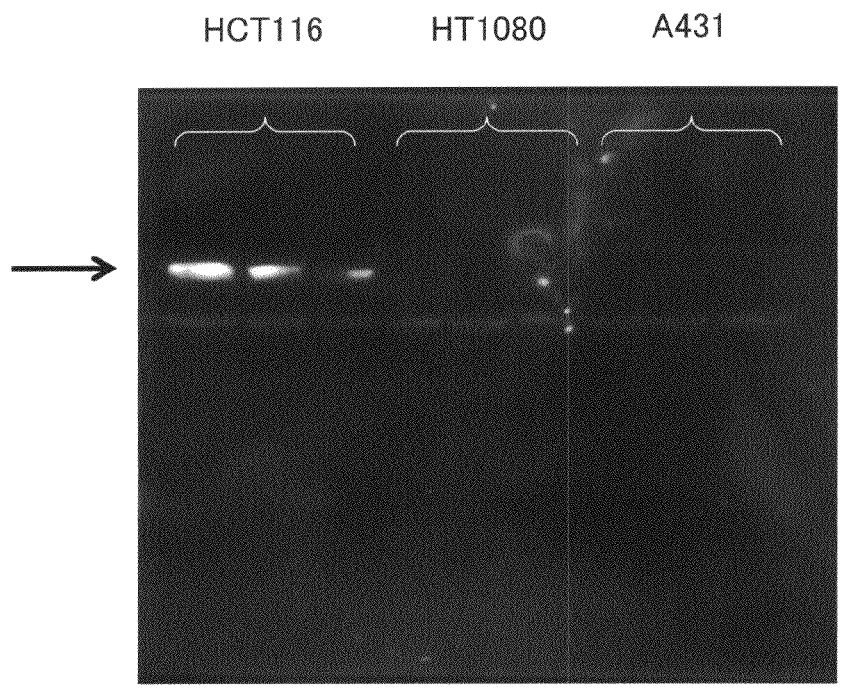
FIG. 3 is a picture showing the SDS-PAGE results of proteins extracted from murine tumor tissue; these results were obtained using proteins extracted from tumor sites of animals inoculated with the following various tumor cells, from the left: HCT116 (animal 1), HCT116 (animal 2), HCT116 (animal 3), HT1080 (animal 4), HT1080 (animal 5), HT1080 (animal 6), A431 (animal 7), A431 (animal 8), and A431 (animal 9).
Figure 4:
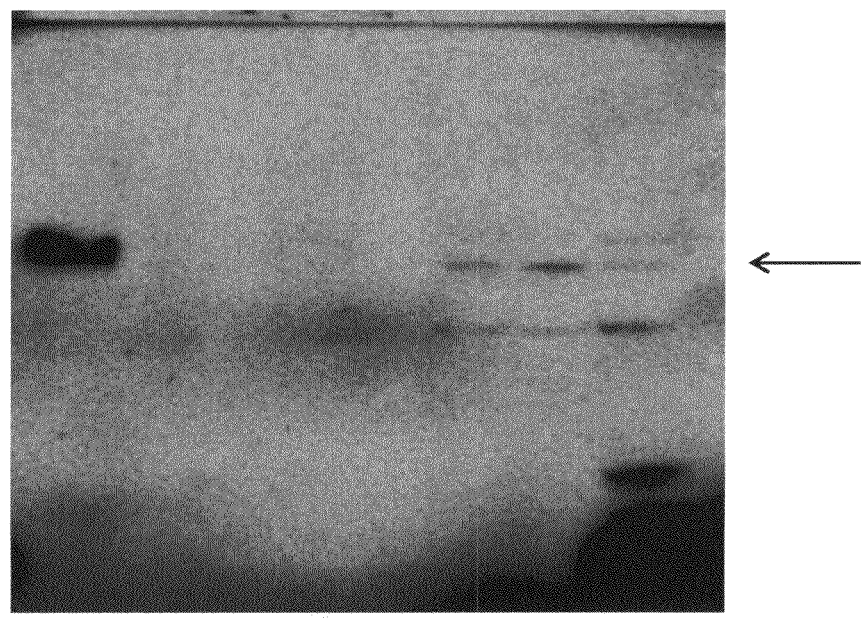
FIG. 4 is a picture showing the SDS-PAGE results of proteins extracted from tumors and the thigh tissue of mice in which tumors were formed by inoculation with HCT116 cells; from the left: standard specimen (human SPARC), thigh-extracted liquid (animal 10), thigh-extracted liquid (animal 11), thigh-extracted liquid (animal 12), tumor-extracted liquid (animal 10), tumor-extracted liquid (animal 11), and tumor-extracted liquid (animal 12).

From the results of FIGS. 2, 3, and 4, it can be understood that compounds exhibiting an albumin-binding property, including the compounds of the present invention having the structure represented by general formula (1), were able to selectively image sites expressing SPARC.

Effect of the Invention

The present invention provides a novel cyanine compound. The cyanine compound tends to accumulate in diseased parts, such as tumors, and is suitable as an imaging component in a near infrared fluorescence imaging agent. The near infrared fluorescence imaging agent containing the compound of the present invention is characterized by outlining tumors for extended periods.

The invention claimed is:
1. A compound represented by general formula (II) below, or a pharmacologically acceptable salt thereof:

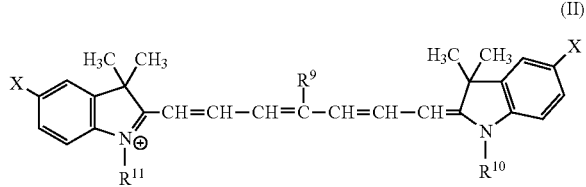

wherein X represents a sulfonic acid group; each of $R^{10}$ and $R^{11}$, which may be identical or different, represents an alkyl group substituted with a sulfonic acid group, and $R^9$ represents a phenyl group.

2. A compound represented by general formula (II) below, or a pharmacologically acceptable salt thereof:

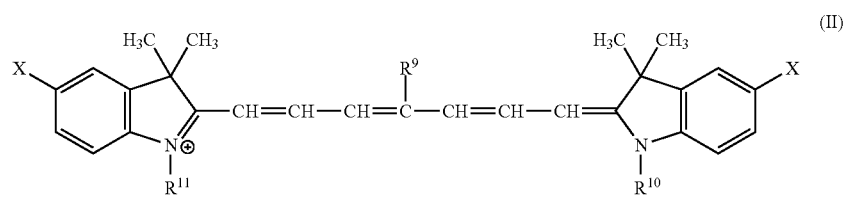

wherein X represents a sulfonic acid group; each of $R^{10}$ and $R^{11}$, which may be identical or different, represents an alkyl group substituted with a sulfonic acid group, and $R^9$ represents a benzyl group.

3. A compound represented by general formula (II) below, or a pharmacologically acceptable salt thereof:

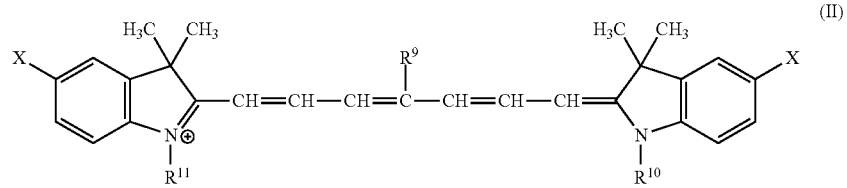

wherein X represents a sulfonic acid group; each of $R^{10}$ and $R^{11}$, which may be identical or different, represents an alkyl group substituted with a sulfonic acid group, and $R^9$ represents a 4-pyridyl group.

4. A compound represented by general formula (II) below, or a pharmacologically acceptable salt thereof:

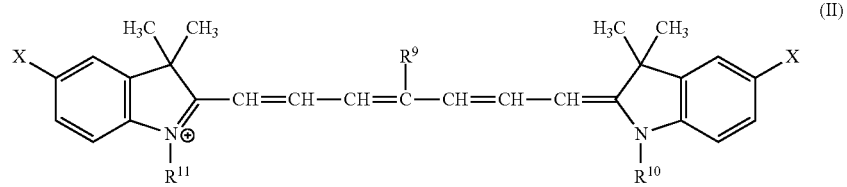

wherein X represents a sulfonic acid group; each of $R^{10}$ and $R^{11}$, which may be identical or different, represents an alkyl group substituted with a sulfonic acid group, and $R^9$ represents an aryl group, an arylalkyl group, a heterocyclic group, an acylamino group, an arylamino group, an N-aryl-N-alkylamino group, an arylthio group, an aryloxy group, or an acylaminoaryloxy group, said compound being selected from the group consisting of the following Compounds 1, 2 and 3:

Compound 1
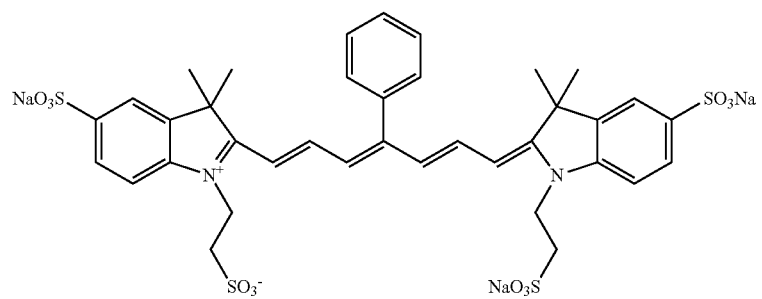
Compound 2
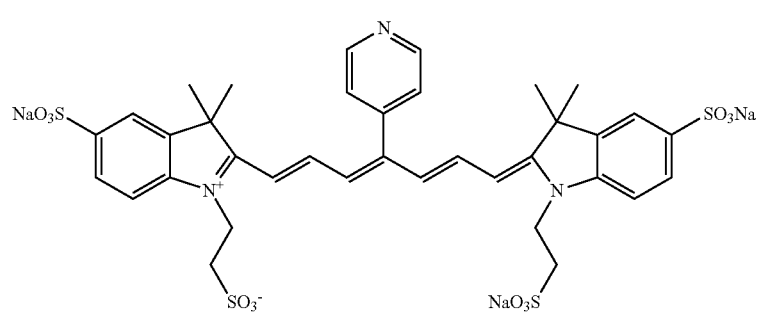
Compound 3
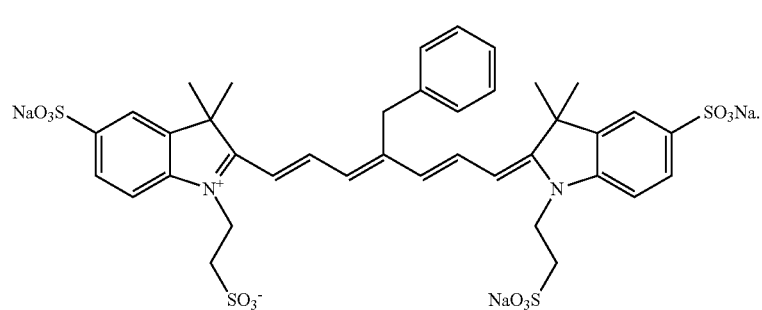
* * * * *